(12) United States Patent
Christensen et al.

(10) Patent No.: US 8,680,271 B2
(45) Date of Patent: Mar. 25, 2014

(54) PROCESS FOR SYNTHESIZING 6-BROMO-3-1-(1-METHYL-1H-PYRAZOL-4-YL)-5-(3(R)-PIPERIDINYL)PYRAZOLO [1,5-A]PYRIMIDIN-7-AMINE

(75) Inventors: Melodie D. Christensen, New York, NY (US); Jungchul Kim, Basking Ridge, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/637,187

(22) PCT Filed: Mar. 21, 2011

(86) PCT No.: PCT/US2011/029133
§ 371 (c)(1), (2), (4) Date: Sep. 25, 2012

(87) PCT Pub. No.: WO2011/119457
PCT Pub. Date: Sep. 29, 2011

(65) Prior Publication Data
US 2013/0012707 A1    Jan. 10, 2013

Related U.S. Application Data

(60) Provisional application No. 61/317,971, filed on Mar. 26, 2010.

(51) Int. Cl.
*C07D 487/12* (2006.01)

(52) U.S. Cl.
USPC .......................... 544/280; 544/242; 544/253

(58) Field of Classification Search
USPC ........................................ 544/242, 253, 280
See application file for complete search history.

(56) References Cited

U.S. PATENT DOCUMENTS

| | | | | |
|---|---|---|---|---|
| 6,172,256 B1 * | 1/2001 | Malecha et al. | ................ | 560/38 |
| 6,900,225 B2 * | 5/2005 | Takemura et al. | ............ | 514/312 |
| 7,119,200 B2 * | 10/2006 | Guzi et al. | ..................... | 544/281 |
| 7,161,003 B1 * | 1/2007 | Guzi et al. | ..................... | 544/281 |
| 7,196,078 B2 | 3/2007 | Guzi et al. | | |
| 7,605,155 B2 * | 10/2009 | Guzi et al. | ..................... | 514/218 |
| 2004/0142957 A1 | 7/2004 | Takemura et al. | | |

FOREIGN PATENT DOCUMENTS

EP    1 156 999 B1    11/2004

* cited by examiner

*Primary Examiner* — Golam M M Shameem
(74) *Attorney, Agent, or Firm* — Richard S. Parr; Laura M. Ginkel

(57) ABSTRACT

A process for the preparation of the compound of Formula (I) is described.

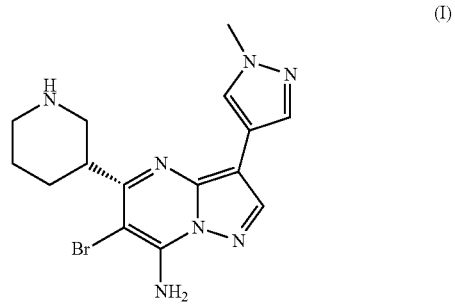

(I)

1 Claim, No Drawings

PROCESS FOR SYNTHESIZING 6-BROMO-3-1-(1-METHYL-1H-PYRAZOL-4-YL)-5-(3(R)-PIPERIDINYL)PYRAZOLO[1,5-A]PYRIMIDIN-7-AMINE

FIELD OF THE INVENTION

The present invention relates to a process for the preparation of the compound of Formula I

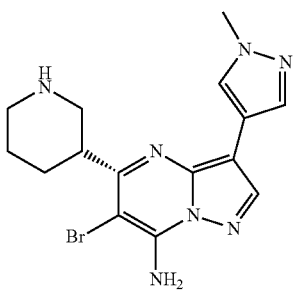

I 6-bromo-3-(1-methyl-1H-pyrazol-4-yl)-5-(3(R)-piperidinyl)pyrazolo[1,5-a]pyrimidin-7-amine, which has been shown to be useful in the treatment of various cancers. The IUPAC name of the compound of Formula I is 6-bromo-3-(1-methyl-1H-pyrazol-4-yl)-5-[(3R)-piperidin-3-yl]pyrazolo[1,5-a]pyrimidin-7-amine.

BACKGROUND

Identification of any publication in this section or any section of this application is not an admission that such publication is prior art to the present invention.

The compound of Formula I is generically and specifically disclosed in U.S. Pat. No. 7,196,078, incorporated herein by reference. This compound, named SCH 900776, is disclosed to be in clinical trials for the treatment of various cancers. See, for example, https://partnering.thomson-pharma.com/partnering/partnering/JAVA_REPORTS.CALL_JAVA_REPORT?entity_id=61956&entity_type=Drug.

Processes suitable for making the compound of Formula I are generally described in the '078 patent. In the '078 patent, the compound of Formula I is reported to be prepared, in the disclosed final step of the synthesis, by deprotecting the N-Boc derivative of Formula A by using trifluroacetic acid ("TFA") in $CH_2Cl_2$, followed by treatment with $Na_2CO_3$ in a mixture of $CH_2Cl_2$ and methanol:

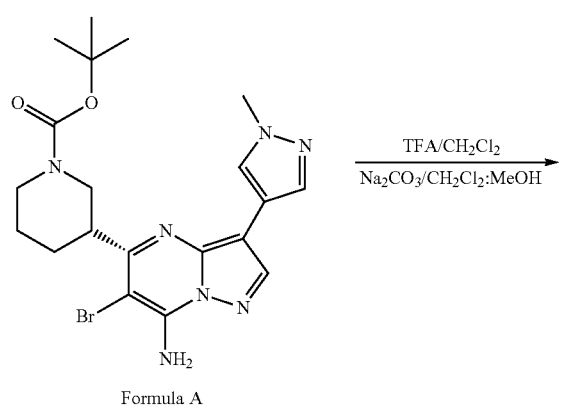

Formula A

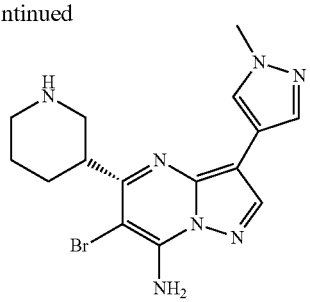

Formula I

It will be environmentally friendly to use a process that avoids the use of $CH_2Cl_2$ particularly for large scale manufacturing. It will be an added advantage if one could obtain high yields of a high purity product.

In the present process, the compound of Formula A is deprotected to yield the compound of Formula I by using ethanolic HCl, followed by treatment with KOH:

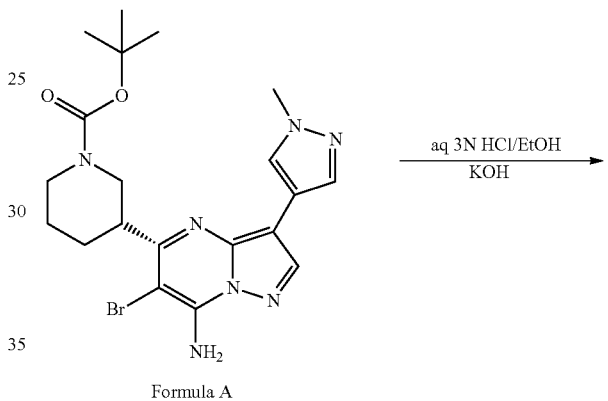

Formula A aq 3N HCl/EtOH
―――――――→
KOH

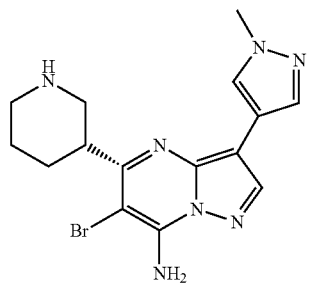

Formula I

SUMMARY AND DESCRIPTION OF THE INVENTION

The present invention is a process for preparing the compound of Formula I (SCH 900776)

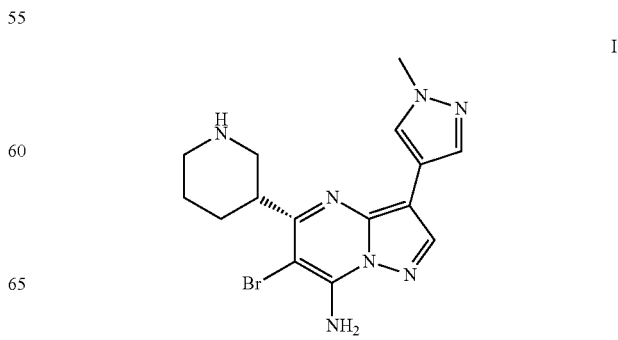

I comprising:

1) treating the compound of Formula A with an acid, such as for example, alcoholic HCl for about 30 minutes-4 hrs at about 25-70° C.;

2) adjusting the final pH to about 10-11 using a suitable base, such as for example, KOH;

3) adding a suitable solvent such as for example, ethanol, and heating, if necessary, to a temperature of 50-80° C. for about 10-120 minutes;

4) cooling to below reflux temperature and isolating the compound of Formula I.

Additional improvements can be made if necessary such as, for example, seeding with crystals etc. Such improvements are within the knowledge of one with ordinary skill in the art.

In one non-limiting embodiment, the present inventive process is illustrated in the Example shown below:

| Material | M.W. | Eq. | Amount | Mole | X | |
|---|---|---|---|---|---|---|
| Formula A | 476.37 | 1.00 | 10.0 kg | 18.9 | 1X | kg |
| 37% aq HCl | N/A | 6.08 | 12.5 L | 135 | 1.25X | L |
| EtOH | N/A | N/A | 170 L | N/A | 17X | L |
| USP Water | N/A | N/A | 207 L | N/A | 20.7X | L |
| KOH Pellets | N/A | 8.95 | 10.5 kg | N/A | 1.05X | kg |

1. A mixture of 1×kg the compound of Formula A, 5×L EtOH and 5×L 3N aq HCl was agitated for 1.5 hours at 50° C.

HCl Solution Preparation: Dilute 1.25×L 37% HCl solution with 3.75×L water.

2. It was then sampled for In-Process Control: Formula A≤0.5% LC Area (For sample Prep, a 0.25 ml aliquot was dissolved in 100 ml Acetonitrile:Water).

Agitation was continued, if needed, for an additional 1 hour and sampled again.

3. The batch pH was adjusted to between 5-7 using 15% KOH (Charge about 4.0×L) at 50° C.

For KOH Solution Preparation, 1.05×kg KOH pellets were dissolved in 5.95×L water.

4. 12×L ethanol was added to the reaction mixture while maintaining batch temperature at 50° C.

5. The batch was heated to reflux (78° C.).

6. The pH was adjusted to be between 10.0-11.0 by adding 0.5×L 15% KOH.

7. It was then cooled to 72° C. (at 0.3° C./min) over 20 minutes.

8. It was then seeded with the compound of Formula I (0.008×).

9. It was the held at 72° C. for 45 minutes.

10. The it was cooled to 5° C. (0.3° C./min) over 4 hours.

11. 3× water was added while maintaining batch temperature at 5° C.

12. It was then held at 5° C. for an hour.

13. The wet cake was filtered and washed with 20× water in 3 shots of 6.6×.

14. The wet cake was dried under vacuum at 25° C. to give 0.7×-0.8× of the compound of Formula I.

15. It was dried until the moisture content (measured by, for example, Karl Fisher)≤6.0% and EtOH≤0.1%.

16. The dry cake was sampled for HPLC (15 mg dry cake was dissolved in 100 ml 1:1 Acetonitrile:Water).

HPLC Purity was 98-100%.

17. The dry cake was sampled for chiral HPLC (50 mg dry cake was dissolved in 100 ml EtOH).

18. The wt/wt % purity was determined by NMR assay (Solvent: MeOD).

19. The filtrate was sampled for any additional compound of Formula I (0.5 ml aliquot was dissolved in 10 ml 1:1 Acetonitrile:Water).

Typical yield was about 90% (mole percent) based on the compound of Formula A, and the HPLC based purity about 98-100%.

We claim:

1. A process for preparing the compound of Formula I comprising:

1) treating the compound of Formula A with alcoholic HCl for about 30 minutes-4 hrs at about 25-70° C.;

2) adjusting the pH to about 10-11 using KOH;

3) adding ethanol, and heating to a temperature of 50-80° C. for about 10-120 minutes;

4) cooling to below reflux;

5) optionally seeding with the compound of Formula I; and 6) isolating the compound of Formula I.

* * * * *